(12) United States Patent
Leen

(10) Patent No.: US 11,846,747 B2
(45) Date of Patent: Dec. 19, 2023

(54) GAS SAMPLING INSTRUMENTS AND METHODS

(71) Applicant: ABB Schweiz AG, Baden (CH)

(72) Inventor: J. Brian Leen, Sunnyvale, CA (US)

(73) Assignee: ABB Schweiz AG, Baden (CH)

( * ) Notice: Subject to any disclaimer, the term of this patent is extended or adjusted under 35 U.S.C. 154(b) by 584 days.

(21) Appl. No.: 16/548,950

(22) Filed: Aug. 23, 2019

(65) Prior Publication Data

US 2021/0055451 A1    Feb. 25, 2021

(51) Int. Cl.
*G01V 9/00* (2006.01)
*G01N 1/22* (2006.01)
*G01N 33/00* (2006.01)
*G01N 1/24* (2006.01)

(52) U.S. Cl.
CPC ........... *G01V 9/007* (2013.01); *G01N 1/2273* (2013.01); *G01N 1/24* (2013.01); *G01N 33/0014* (2013.01)

(58) Field of Classification Search
CPC .. G01M 3/38; G01M 3/20; G01F 1/00; G01N 1/2205; G01N 1/2294; G01N 2001/2267; G01N 2001/4016; G01N 2021/1793; G01N 33/0075; G01S 17/95; G01W 1/00; Y02A 90/10
See application file for complete search history.

(56) References Cited

U.S. PATENT DOCUMENTS

| | | |
|---|---|---|
| 4,135,092 A | 1/1979 | Milly |
| 4,159,635 A | 7/1979 | Sehmel |
| 4,226,115 A | 10/1980 | Williams |
| 4,764,186 A | 8/1988 | Langer |
| 5,297,421 A | 3/1994 | Hosonuma et al. |
| 6,518,562 B1 | 2/2003 | Cooper et al. |
| 6,724,481 B2 | 4/2004 | Makino et al. |
| 6,785,619 B1 | 8/2004 | Homann et al. |
| 7,375,814 B2 | 5/2008 | Reichardt et al. |

(Continued)

FOREIGN PATENT DOCUMENTS

| | | |
|---|---|---|
| EP | 0 448 360 A1 | 9/1991 |
| FR | 2831665 A1 | 5/2003 |

(Continued)

OTHER PUBLICATIONS

Jakuba, "Stochastic Mapping for Chemical Plume Source Localization with Application to Autonomous Hydrothermal Vent Discovery", downloaded from https://dspace.mit.edu/bitstream/handle/1721.1/38931/166142007-MIT.pdf?sequence=2, Apr. 19, 2007, 325 pages.

(Continued)

*Primary Examiner* — Harshad R Patel
*Assistant Examiner* — Gedeon M Kidanu
(74) *Attorney, Agent, or Firm* — Armstrong Teasdale LLP

(57) ABSTRACT

Devices, systems, and methods for sampling of gases to determine information regarding leaks are disclosed. Balanced sampling can be achieved by application of an inlet having a gas permeable membrane covering the opening. Extending the opening for a length can provide additional coverage for gas sampling. Connection of gas sampling instruments with analysis systems can determine leak information for use in remedying leaks, for example, from industrial equipment such as pipelines.

18 Claims, 3 Drawing Sheets

(56) References Cited

U.S. PATENT DOCUMENTS

| | | | |
|---|---|---|---|
| 8,032,123 B2 | 10/2011 | Sakhpara | |
| 8,294,899 B2* | 10/2012 | Wong | G01S 17/95 |
| | | | 250/338.5 |
| 8,312,780 B2* | 11/2012 | Blacklin | G01N 1/10 |
| | | | 73/863 |
| 8,781,755 B2 | 7/2014 | Wong | |
| 9,435,782 B2* | 9/2016 | Lenz | G01N 33/0075 |
| 9,482,591 B2 | 11/2016 | Rella et al. | |
| 9,494,511 B2 | 11/2016 | Wilkins | |
| 9,500,556 B2 | 11/2016 | Rella et al. | |
| 9,557,240 B1 | 1/2017 | Tan et al. | |
| 9,618,417 B2 | 4/2017 | Rella et al. | |
| 9,719,879 B1 | 8/2017 | Tan et al. | |
| 9,978,251 B2 | 5/2018 | Gonia et al. | |
| 10,119,890 B2* | 11/2018 | Massengale | G01N 1/2247 |
| 10,161,825 B2 | 12/2018 | Rella et al. | |
| 10,345,200 B2 | 7/2019 | Scialo | |
| 2004/0050188 A1 | 3/2004 | Richards et al. | |
| 2007/0261503 A1* | 11/2007 | Zimmer | G01N 1/2205 |
| | | | 73/863.23 |
| 2007/0266800 A1* | 11/2007 | Risk | G01N 33/24 |
| | | | 73/863.23 |
| 2008/0045156 A1 | 2/2008 | Sakhpara | |
| 2010/0050750 A1 | 3/2010 | Saaski | |
| 2010/0091267 A1* | 4/2010 | Wong | G01S 15/885 |
| | | | 356/438 |
| 2010/0199787 A1 | 8/2010 | Gauthier | |
| 2010/0212436 A1 | 8/2010 | Swenson | |
| 2011/0247400 A1* | 10/2011 | Schwartz | G01M 3/38 |
| | | | 73/40.7 |
| 2012/0028820 A1 | 2/2012 | Rhodes et al. | |
| 2012/0092649 A1 | 4/2012 | Wong | |
| 2013/0110400 A1 | 5/2013 | Moshe | |
| 2013/0220036 A1 | 8/2013 | Faust | |
| 2013/0291622 A1 | 11/2013 | Heinemeyer | |
| 2014/0318276 A1 | 10/2014 | Cappa et al. | |
| 2015/0047416 A1 | 2/2015 | Rella | |
| 2016/0146696 A1 | 5/2016 | Steele et al. | |
| 2018/0172544 A1* | 6/2018 | MacMullin | G01M 3/38 |

FOREIGN PATENT DOCUMENTS

| | | |
|---|---|---|
| KR | 101041531 B1 | 6/2011 |
| RU | 2519405 C1 | 6/2014 |
| SU | 292097 A1 | 1/1971 |
| SU | 1366908 A1 | 1/1988 |
| WO | 2010/070147 A1 | 6/2010 |
| WO | 2015/052421 A1 | 4/2012 |

OTHER PUBLICATIONS

"Bio-Inspired and Probabilistic Algorithms for Distrubed Odor Source Localization using Mobile Robots", downloaded from https://infoscience.epfl.ch/record/143049/files/EPFL_TH4628.pdf, 2010, 6 pages.

Ishida et al.., "Remote sensing of gas/odor source location and concentration distribution using mobile system", Sensors and Actuators B 49 (1998) 52-57.

Reggente et al., "Using Local Wind Information for Gas Distribution Mapping in Outdoor Environments with a Mobile Robot", IEEE Sensors 2009 Conference, pp. 1715-1720.

Fukazawa et al., "Estimating Gas-Source Location in Outdoor Environment Using Mobile Robot Equipped with Gas Sensors and Anemometer", IEEE Sensors 2009 Conference, pp. 1721-1724.

Neumann et al., "Autonomous Gas-Sensitive Microdrone", IEEE Robotics & Automation Magazine, Mar. 2012, pp. 50-61.

Lilienthal, "Chapter 10, Improved Gas Source Localization with a Mobile Robot by Learning Analytical Gas Dispersal Models from Statistical Gas Distribution Maps Using Evolutionary Algorithms", IGI Global, pp. 249-276.

McManus et al., "Field measurement of atmospheric methane with a HeNe laser-based real-time instrument", downloaded from https://www.spiedigitallibrary.org/conference-proceeings-of-spie on Mar. 20, 2019, 14 pages.

Hirst et al., "Oil and gas prospecting by ultra-sensitive optical gas detection with inverse gas dispersion modelling", Geophysical Research Letters, vol. 31, L12115, 2004, 4 pages.

"GIS for Petroleum", downloaded from www.ESRI.com/petroleum, Feb. 2007, 32 pages.

Thomson et al., "An improved algorithm for locating a gas source using inverse methods", Atmospheric Environment 41 (2007) 1128-1134.

Lamb et al., "Development of Atmospheric Tracer Methods to Measure Methane Emissions from Natural Gas Facilities and Urban Areas", Envir. Sci. Technol. 1995, 29, 1468-1479.

Leifer et al., In situ sensing of methane emissions from natural marine hydrocarbon seeps A potential remote sensing technology, Earth and Planetary Science Letter 245 (2006) 509-522.

Horst et al., "Footprint Estimation for Scalar Flux Measurements in the Atmospheric Surface Layer", Boundary-Layer Meteorology 59:279-296, 1992.

Lochmatter et al., "Tracking Odor Plumes in a Laminar Wind Field with Bio-Inspired Algorithms", Springer Tracts in Advanced Robotics, Nov. 2008, 16 pages.

Cabrita et al., "Odor guided exploration and plume tracking—Particle Plume Explorer", 6 pages.

Bennetts et al., "Mobile robots for localizing gas emission sources on landfill sites: is bio-inspiration the way to go?", fronteirs in Neuroengineering, Jan. 2012, vol. 4, Article 20, 12 pages.

Meng et al., "Collective Odor Source Estimation and Search in Time-Variant Airflow Environments Using Mobile Robots", Sensors 2001, 11, 29 pages.

Pavlin et al., "Gas Detection and Source Localization: A Bayesian Approach", 2011 IEEE, 8 pages.

Baetz et al., "Mobile Robots with Active IR-Optical Sensing for Remote Gas Detection and Source Localization", 2009 IEEE International Conference on Robotics and Automation, pp. 2773-2778.

Ishida et al., "Remote Sensing and Localization of Gas/Odor Source and Distribution Using Mobile Sensing System", TRASDUCERS '97, 1997 International Conference on Solid-State Sensors and Actuators, pp. 559-563.

Ishida et al., "Three-Dimensional Gas-Plume Tracking Using Gas Sensors and Ultrasonic Anemometer", 2004 IEEE, pp. 1175-1178.

Ishida et al., "Mobile Robot Path Planning Using Vision and Olfaction to Search for a Gas Source", 2005 IEEE, pp. 1112-1115.

Jiang et al., "A Novel Object Recognition Method for Mobile Robot Localizing a Single Odor/Gas Source in Complex Environments", 2008 IEEE, 5 pages.

Wainner et al., "High Altitude Aerial Natural Gas Leak Detection System", Apr. 2007, 100 pages.

Federal Institute of Industrial Property (ISA/RU), International Search Report and Written Opinion for related PCT/US2020/046412, dated Nov. 19, 2020, 10 pages.

Extended European Search Report issued in European Patent Application No. 20857877.3, dated Jul. 4, 2023, 11 pages.

* cited by examiner

GAS SAMPLING INSTRUMENTS AND METHODS

TECHNICAL FIELD

The present disclosure relates to the field of gas leak detection. More particularly, the present disclosure relates to devices, systems, and methods for gas leak detection.

BACKGROUND

Leakage of materials taking gaseous form can pose complex problems for remediation. Techniques for accurate and/or precise quantification, and/or other investigation, of the leaked gas within the environment can assist in locating and remedying the leak. Yet, factors such as ambient conditions can exacerbate turbulent gas propagation, imposing challenging circumstances for collection and analysis of ambient gas.

SUMMARY

According to one aspect of the present disclosure, a gas sampling instrument for collection of sample gas may comprise an elongated casing having a cavity defined therein, a sample intake opening defined in the elongated casing to receive sample gas into the cavity, the sample intake opening extending for a length along the elongated casing, and a membrane secured to the elongated casing with a seal around the sample intake opening for passing sample gas through the membrane into the cavity. The elongated casing may include at least one port for connection with a gas analysis system, where the at least one port is arranged in fluid communication with the cavity to provide passage for sample gas.

According to another aspect of the present disclosure, a leak detection assembly for detecting a leak source may comprise a gas sampling instrument and a gas analysis system. The gas sampling instrument may comprise an elongated casing having a cavity defined therein, a sample intake opening defined in the elongated casing to receive sample gas into the cavity, the sample intake opening extending for a length along the elongated casing, a membrane secured to the elongated casing with a seal around the sample intake opening for passing sample gas through the membrane into the cavity, and a port arranged in fluid communication with the cavity to provide passage for sample gas. The gas analysis system may be coupled with the port of the gas sampling instrument for receiving sample gas from the cavity for analysis to detect the leak source.

According to yet another aspect of the present disclosure, a method of detecting a leak source may comprise mounting a gas sampling instrument to a vehicle, moving the vehicle and the mounted gas sampling instrument through a geographic area to collect sample gas, and analyzing the collected sample gas to detect the leak source. The gas sampling instrument may comprise an elongated casing having a cavity defined therein, a sample intake opening extending for a length along the elongated casing, and a membrane secured to the elongated casing with a seal around the sample intake opening. Collecting sample gas may comprise passing sample gas through the membrane into the cavity.

These and other features of the present disclosure will become more apparent from the following description of the illustrative embodiments.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
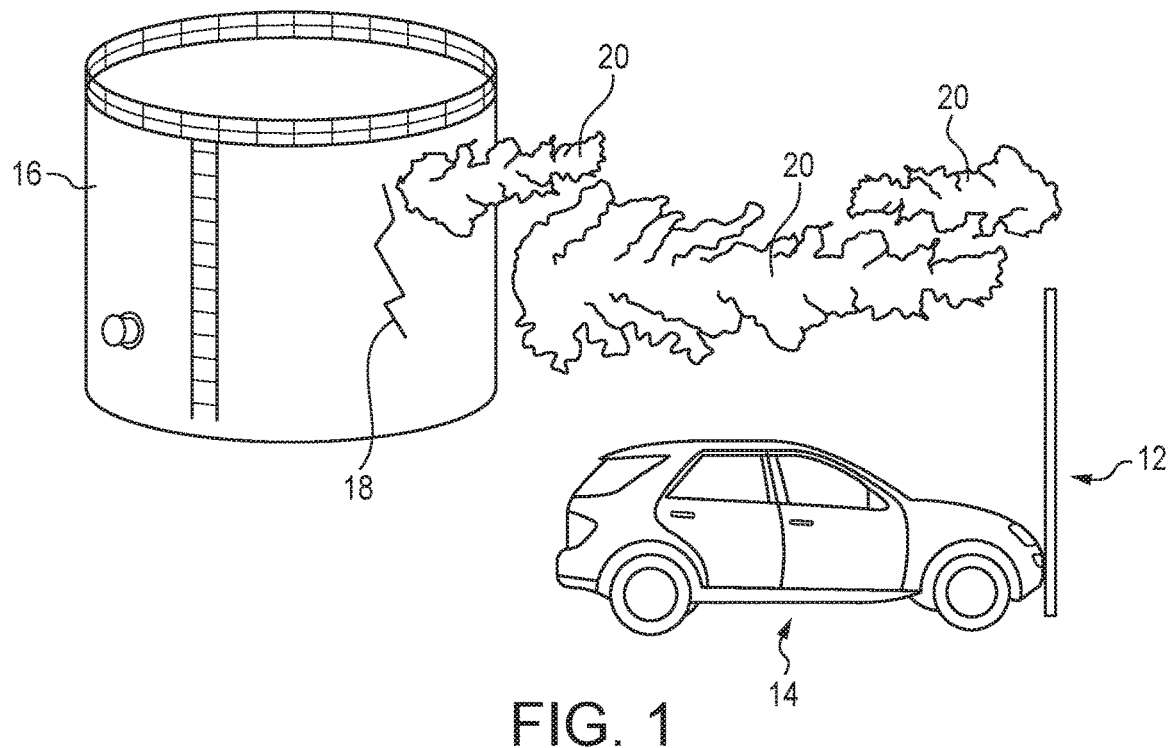
FIG. 1 is a diagrammatic view of an example of a leak from industrial equipment releasing materials which take gaseous form in the ambient environment, showing a number of gaseous plumes to depict plume propagation of the released materials, and showing that a gas sampler is connected with a vehicle for sampling of ambient gases.

While the concepts of the present disclosure are susceptible to various modifications and alternative forms, specific embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Leak control, for example, identifying and resolving leaks from industrial facilities, can present interesting challenges to quickly and/or efficiently remedying leaks. Robust leak detection can assist in locating the source of a leak for remediation. However, leak detection into ambient environments can present challenges to accurately and/or precisely sampling leaked gaseous products. For example, practical obstacles of dispersion of gaseous products into ambient environment can complicate the sample collection and/or analysis process. Such practical obstacles can include a large and/or open physical area into which leaked gaseous products can quickly disperse, for example, outdoors or within a large industrial area. Moreover, in sampling such ambient environments, poor sampling techniques can provide misleading information, which can result in faulty leak source determination and/or inaccurate estimation of the severity of the leak. Accordingly, improved sampling techniques for collecting gaseous samples in ambient environments can enhance leak detection.

In the illustrative embodiment shown in FIG. 1, a gas sampler 12 for gathering samples from the ambient environment is shown mounted to a vehicle 14. The vehicle 14 is illustratively embodied as a car but, in other embodiments, may be another suitable type of vehicle, such as a truck, a utility vehicle, a helicopter, an airplane, a boat, an unmanned aerial vehicle (UAV), an autonomous underwater vehicle (AUV), a bicycle, or a snowmobile. In still other embodiments, the gas sampler 12 and related equipment may be carried by a human operator.

By way of example, a leak source is illustratively shown in FIG. 1 as an industrial process tank 16, having a crack 18 from which tank contents can escape to the environment, although leak sources are not limited by the example and may not necessarily derive from equipment failure. In FIG. 1, the product leaked or leaking from the tank 16 illustratively forms gaseous plumes 20. The gaseous plumes 20 are depicted as partially distinct from each other, arranged at different vertical heights from the ground, as a non-limiting example for descriptive purposes to indicate the diverse range of physical arrangements that gaseous plums may take on when leaked into ambient space, and plumes 20 may be connected with each other. Examples of factors which may affect plume dispersion may include weather, plume chemistry and/or conditions, leak configuration, and/or time of day, among others. Moreover, as suggested in FIG. 2, the path of extension of each plume 20 can be oriented differently from each other, for example, having different propagation trajectories, and can present different sampling conditions for gas samplers. Notably, the gaseous plumes 20 may not themselves be easily visible, for example, the plumes 20 may be partly or wholly invisible to the human eye.

As previously suggested, sampling of gaseous products in the ambient can be susceptible to inaccurate impressions of leaks. Operating gas samplers along the edges of gas plumes and/or in turbulent areas can yield unreliable results, for example, by imposing artificially high and/or low concentration samples. Moreover, as sophisticated analysis of gas samples can be applied to dramatically expand on the information observable from the sample itself, misimpressions created by the sampling technique can lead to faulty conclusions regarding the source of the leak.

The gas sampler 12 is illustratively formed as an elongated member mounted to the front of the vehicle 14 for transport about a geographic area to collect gas samples for analysis. The gas sampler 12 can provide reliable sampling of gas from the environment across a large geographic area, such that the location, source, and/or other conditions of the leak can be efficiently determined for remediation. Although the gas sampler 12 is shown as mounted to the front of the vehicle 14 with vertical orientation, in the centerline of the vehicle 14, in some embodiments, the gas sampler 12 may be oriented in any suitable manner on the vehicle 14, including but without limitation, off-center, partly or wholly horizontally (lateral, front to rear), partly or wholly along any of the roof, sides, or undercarriage. Although the gas sampler 12 is illustratively embodied as generally linear, it is contemplated that, in some embodiments, the gas sampler 12 may be formed with bends or curvature (e.g., curvature conforming with the shape of the vehicle 14). It is also contemplated that the gas sampler 12 may be bent to sample in two or more dimensions (e.g., using a sample intake opening that forms an extended two-dimensional surface). For example, a gas sampler 12 with a 90-degree bend could be used to sample laterally as well as vertically.

Figure 3:
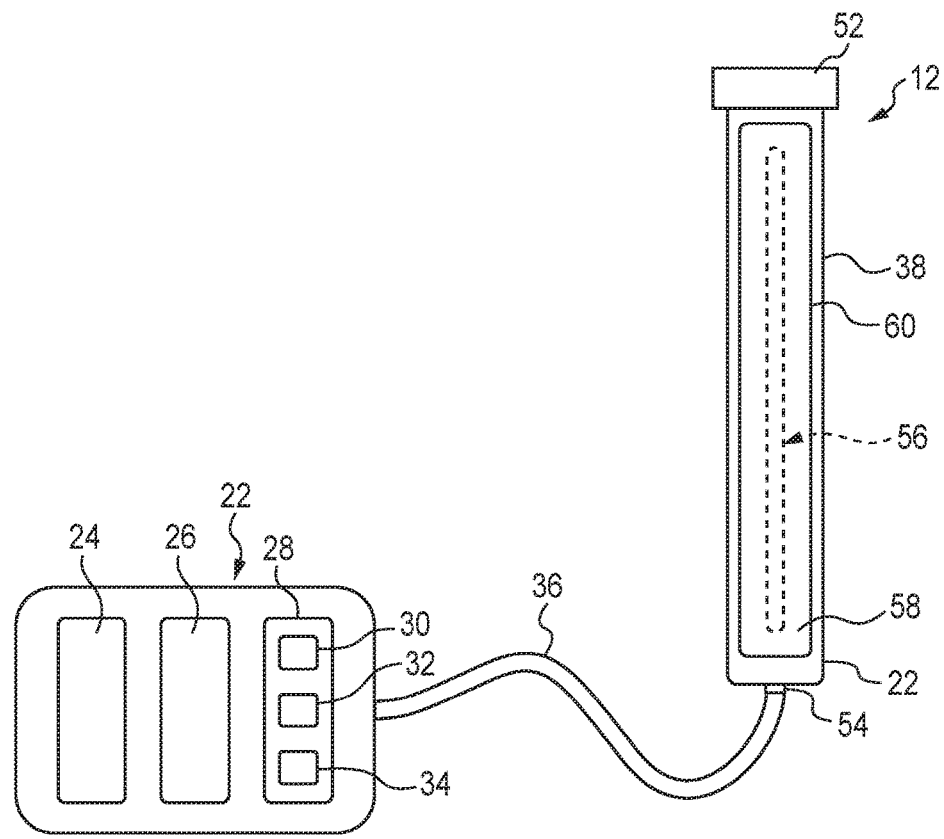
FIG. 3 is an elevation view of a leak detection assembly including a gas analyzer connected with the gas sampler to receive gaseous samples from the ambient environment for analysis.

Referring now to FIG. 3, the gas sampler 12 is shown in communication with a gas analysis system 22 via a sampling hose 36. The gas analysis system 22 is illustratively embodied as a self-contained gas sample analyzer which can be mounted on the vehicle 14 to preform sample analysis to support determination of conditions of the leak. For example, the gas analysis system 22 may analyze sample gas to detect and/or characterize the leak source. The gas analysis system 22 illustratively comprises a sampling system 24, an analysis system 26, and a control system 28 for directing sampling and analysis operations.

The sampling system 24 illustratively includes a vacuum pump and related components for drawing gas samples from the gas sampler 12 via the sampling hose 36. The analysis system 26 includes gas sample analyzing features 27 such as optical (e.g., laser), physical (e.g., temperature, humidity), and/or chemical analysis devices for conducting related gas sample analysis operations, and ambient analyzing features 29 such as ambient condition sensors for temperature, wind speed and/or direction, humidity, etc. Illustrative examples of suitable analysis systems are disclosed in U.S. Pat. Nos. 5,297,421 and 9,557,240, U.S. Patent Application Publication Nos. 2008/0045156 and 2010/0091267, and PCT International Application Publication No. WO 2010/070147, the entire contents of which are each incorporated herein by reference. The gas analysis system 22 illustratively includes a user interface 31, embodied as a graphical touch screen interface for receiving user inputs and communicating analysis information to the user. In other embodiments, any suitable manner of user interface may be applied.

The control system 28 illustratively includes a processor 30 which can execute instructions stored on a memory 32, and communication circuitry 34 for communicating commands of the processor 30 with the sampling system 24 and/or the analysis system 26 for performing sampling and analysis operations, and with the user interface 31 for communication with the user. The processor 30 is illustratively embodied as a microprocessor, but in some embodiments may include any suitable processing unit. The memory 32 is illustratively formed a flash memory device, but in some embodiments, may include any suitable memory storage element, including but without limitation, primary storage and/or non-primary storage (e.g., secondary, tertiary, etc. storage); may include permanent, semi-permanent, and/or temporary storage; and/or may include memory storage devices including but not limited to hard drives (e.g., magnetic, solid state), optical discs (e.g., CD-ROM, DVD-ROM), RAM (e.g., DRAM, SRAM, DRDRAM), ROM (e.g., PROM, EPROM, EEPROM, Flash EEPROM), volatile, and/or non-volatile memory.

Figure 4:
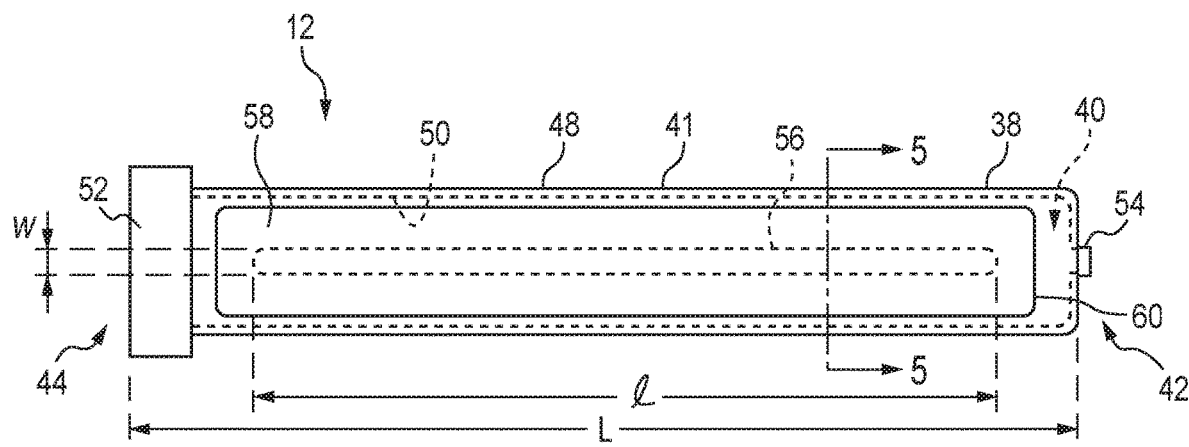
FIG. 4 is closer elevation view of the gas sampler of FIGS. 1-3 showing that the gas sampler includes an elongated inlet covered by a membrane to require gas to pass through the membrane to enter the sampler.

Referring to FIG. 4, the gas sampler 12 illustratively includes an elongated casing 38 that defines a cavity 40 therein. The casing 38 is illustratively embodied as a cylindrical tube having elongated length L between longitudinal ends 42, 44. The casing 38 includes a wall 46 having an exterior surface 48 and an interior surface 50 that defines the cavity 40. In other embodiments, the wall 46 may be one of four walls defining a rectangular (e.g., square) cross-section of the casing 38. In still other embodiments, the casing 38 may have different cross-section shapes with any number of walls 46. The casing 38 illustratively includes a cap 52 enclosing one end 44 of the casing 38 and a communication port 54 on the other end 42 for communication with the gas analysis system 22.

The casing 38 includes an opening 56 formed as an intake for receiving gaseous samples from the environment. The opening 56 is illustratively embodied as an elongated slit having length l extending between the longitudinal ends 42, 44 of the casing 38 with a consistent width w. In some embodiments, the opening 56 may be formed to have any suitable size and/or shape. For example, in some embodiments, the opening 56 may have a variable width w along the length l (which may provide non-uniform gas sample weighting along the length l). The opening 56 is formed as a penetration through the wall 46 for collection of gaseous products from the ambient into the cavity 40 of the casing 38. In other embodiments, the casing 38 may include a plurality of rigid supports (e.g., a wire frame) defining the cavity 40, and the opening 56 may be defined between two of the plurality of rigid supports.

The gas sampler 12 includes a membrane 58 arranged to cover the opening 56. The membrane 58 is illustratively embodied as a sheet of gas permeable material, for example but without limitation, a fabric, for passing gaseous products from the environment therethrough in order to enter the opening 56 and the cavity 40. The membrane 58 is illustratively arranged over the entire opening 56 to require sample gas to pass through the sheet as a flow regulator to restrict the volume of flow into the cavity 40 along the length l of the opening 56. Arrangement of the membrane 58 covering the opening 56 can allow balancing of the flow of gas entering the cavity 40, and can avoid misimpressions of the ambient gas, particularly in sampling along a wide swath, such as that provided by the elongated casing 38.

The communication port 54 is fluidly connected with the cavity 40 to communicate gas samples from the cavity 40 through the communication port 54. The communication port 54 is configured for connection with the gas analysis system 22 via the sampling hose 36 22 to provide gas samples from the cavity 40 for analysis. Vacuum pressure communicated from the gas analysis system 22 (or a vacuum pump) via the hose 36 creates vacuum within the cavity 40 to draw gaseous samples from the ambient environment through the membrane 58, into the cavity 40, and out through the communication port 54. The elongated opening 56 covered with the membrane 58 can provide balanced sampling of environmental gaseous products along the opening 56 while avoiding inaccuracies that can occur from practical challenges such as operating gas samplers along the edges of gas plumes and/or in turbulent areas. Accordingly, gas quantification techniques can be improved in accuracy and/or precision.

Figure 5:
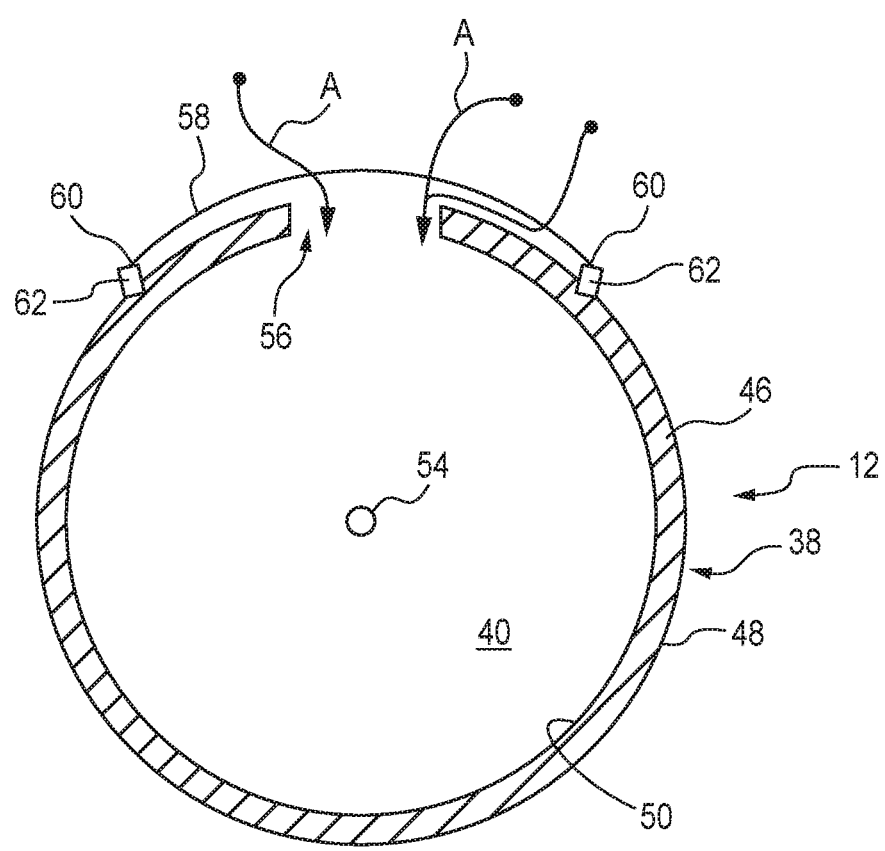
FIG. 5 is a cross-section view of the gas sampler of FIGS. 1-4, taken along the line 5-5 in FIG. 4 showing that the membrane seals with the casing of the sampler to avoid leakage into the casing without passage through the membrane.

Referring to FIG. 5, the membrane 58 is illustratively connected with the casing 38. An outer edge 60 of the membrane 58 is secured with the exterior surface 48 of the wall 46 to form a seal 62 circumferentially about the entire opening 56. By sealing the membrane 58 about the opening 56, the gas entering the opening 56 can be blocked against bypassing of the membrane 58. The gas entering the opening 56 can thus be required to pass through the membrane 58 to assist in accurate and/or precise sampling. By way of example, gaseous particles A can be drawn through the membrane 58, through the opening 56, into the cavity 40, and onto the gas analysis system 22.

The membrane 58 is illustratively formed of a gas permeable, waterproof material. Examples of suitable materials for membrane 58 may include polytetrafluoroethylene (PTFE), silicone (e.g., polydimethylsiloxane (PDMS)), polypropylene, and/or other plastics, and may include products such as Tyvek®, Gortex®, eVent, or the like. Water impermeable materials, such as Teflon AF 2400 and the like, could be used in aqueous environments (e.g., to sample plumes within water columns). Although illustrated in FIG. 5 as a single thin layer, the membrane 58 may comprise any suitable thickness and/or number of layers, including combinations of layers chemically-specific transfer properties to provide chemically-specific sampling.

Within the present disclosure, detection and quantification of gas dispersed through the atmosphere can create problems in many industries. One or more gases can propagate from a source, and can be turbulently mixed into the air. Such gases can take on extended and chaotic structures that move and/or change with time. Existing approaches to detecting these fluctuating plumes may use collectors with either a single inlet or an array of inlets to sample the plume for analysis by a sensor. These approaches can present problems in reliable analysis. For example, single collector inlets can miss the plume and/or transect a non-representative cross section of the plume, while multiple inlets may under sample, and/or can require balancing of the inlets to ensure quantitative results.

Devices, systems, and methods of the present disclosure can avoid such challenges. For example, use of a single membrane inlet with an extended length can assist in balancing the sample technique. Extended inlets can simultaneously sample gases along the length and can improve the probability of detecting plumes. Additionally, applying membranes with gas permeability that is uniform over its length (and/or width), the need to balance flow through multiple inlets can be reduced.

Many industries may need to detect, characterize, locate, and/or quantify gases leaked into the air. In some cases, gas can be detected downwind using sensitive analyzers. For example, natural gas pipelines may be inspected with leak detection from a mobile platform such as a car (e.g., MobileGuard), plane, unmanned aerial system, or man portable system. In some cases, a stationary detector is appropriate and the devices, systems, and methods of the present disclosure can include stationary arrangements as well. For example, an extended inlet can provide a customizable fence line survey length. Another example of aspects of the present disclosure may include (mobile and/or fence line) detection of hydrogen sulfide ($H_2S$), which may be continually (constant and/or periodically) monitored at industrial sites to limit the impacts of releases on the health of surrounding communities.

Detection of gas releases can be complicated by atmospheric turbulence. When gas is carried downwind, it can turbulently mix with the air, resulting in a gas plume that moves in space and time. Mobile measurements can achieve detection by driving downwind of the source, but can sometimes be frustrated by the wind blowing the plume completely away from a (simple) point inlet. Quantification of the amount of gas leaked (flux) can be highly difficult and/or can require that the sampler collects a concentration maxima of the plume—and traversing the side or edge of the plume can result in an underestimation of the leak magnitude.

In the natural gas pipeline example, single inlet sampling systems can be subject to high variability and may increase the likelihood of sampling only an edge of the plume. Multiple inlets can mitigate this edge-sampling concern to some extent but can be expensive to manufacture (e.g., many fittings) and can present difficulties in balancing the inlet flows, which can be critical to accurately measuring the flux. Additionally, clogs and/or obstructions to flow might not be easily noticed during operation of multiple inlet arrangements which can result in changing estimates of flux over a measurement period.

Devices, systems, and methods within the present disclosure can provide solutions to plume edge-sampling, cost, and/or balancing issues, applying a single inlet comprises an extended membrane. In illustrative embodiments a pipe may include a slit along one side, which can be covered in membrane material and sealed along the edges to prevent gas from entering except through the membrane pores. One end of the pipe can be capped while a modest vacuum is applied to the other by the gas analyzer or a sampling system. The vacuum can ensure that gas is uniformly drawn from the length of the membrane. The uniform sampling along the entire membrane surface thus can provide an integrated sample of the plume encountered by the extended membrane inlet.

Figure 2:
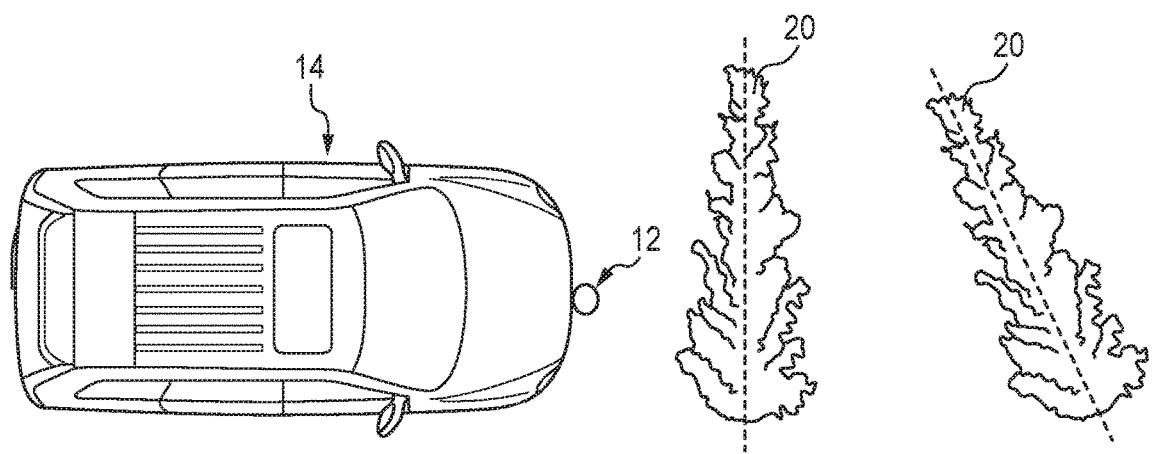
FIG. 2 is a plan view of the vehicle and gas sampler of FIG. 1, showing that gaseous plumes in the ambient environment may be oriented in various ways.

For detection and quantification of a gas source using a mobile platform, the extended membrane inlet may be preferably oriented perpendicular to the direction of driving and perpendicular to the direction of wind propagation as suggested in FIGS. 1 and 2 where the inlet is oriented vertically. In the illustrative embodiment, those gas samples which are admitted through the membrane 58 near an end of the opening 56 opposite from the communication port 54 of the gas sampler 12 in FIG. 3, will take longer to be received by the gas analysis system 22. In some embodiments, however, the angle of the opening 56 may be adjusted to compensate for flow delay along the extended inlet. This may be achieved by matching the forward speed of vehicle 14 with the gas sampler inlet flow speed into the opening 56. Accordingly, changing the angle of the opening 56 relative to the driving direction can allow the adjustment of the matched vehicle velocity. Alternatively, the pumping speed (rate) may be adjusted to match the vehicle's forward speed.

Variability in position of the plume parallel to the drive path can be accounted for by movement (i.e., if the plume is blown further down the road it is just measured later, but still measured). If the plume is lifted or dispersed vertically, the extended inlet can allow sampling and integrating the vertical column to provide a more complete picture of the gas present. Thus, this configuration can effectively capture gas that has diffused vertically and/or horizontally. The collected data can be analyzed using a Gaussian plume model (GPM) fit, alternative gas propagation models, and/or trained regressions. This methodology can be used for a single point inlet in the MobileGuard® system, available from ABB INC. and may also be used with the extended inlet. Gaussian plume fitting and/or regression estimation techniques may be used in determining leak size and/or location based on gas sample data.

In some embodiments, the gas sampler may include bent and/or contoured extended inlet membranes, for example, to conform to the roofline of the vehicle 14. Extended inlet membranes may be formed in cross or star patterns to sample in two dimensions, may extend in 2D to make a sheet inlet, may include multiple parallel membranes (e.g., with a u-turn at one end), may extend along a car bumper as well as vertically. Although the illustrative embodiments include mounting of gas sampler and related component on a vehicle for sampling, in some embodiments, the gas sampler and related components may be portable (e.g., by hand) and/or stationary.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the methods, systems, and articles described herein. It will be noted that alternative embodiments of the methods, systems, and articles of the present disclosure may not include all of the features described yet still benefit from at least some of the advantages of such features. Those of ordinary skill in the art may readily devise their own implementations of the methods, systems, and articles that incorporate one or more of the features of the present disclosure.

The invention claimed is:

1. A gas sampling instrument for collection of a sample gas from at least a portion of a plume of gas, the gas sampling instrument comprising:
    a hollow elongated casing having a sidewall and a cavity, the cavity defined within the hollow elongated casing, the sidewall at least partially enclosing the cavity, the hollow elongated casing having a first length defined between longitudinal ends of the hollow elongated casing;
    a sample intake opening defined in the sidewall to receive the sample gas into the cavity, the sample intake opening formed as an elongated slit having a second length and a width, the second length extending between the longitudinal ends of the hollow elongated casing, wherein the second length of the elongated slit is greater than the width of the elongated slit; and
    a membrane secured to the sidewall with a seal around the sample intake opening for passing the sample gas through the membrane into the cavity, wherein the membrane is configured to act as a flow regulator that restricts a volume of flow of the sample gas into the cavity along the second length of the sample intake opening to balance the flow of the sample gas entering the cavity, and
    wherein the hollow elongated casing includes at least one port for connection with a gas analysis system, the at least one port arranged in fluid communication with the cavity to provide passage for the sample gas.

2. The gas sampling instrument of claim 1, wherein the sidewall is one of four sidewalls defining a rectangular cross-section of the hollow elongated casing.

3. The gas sampling instrument of claim 1, wherein the hollow elongated casing comprises a plurality of rigid supports defining the cavity, and wherein the sample intake opening is defined between two of the plurality of rigid supports.

4. The gas sampling instrument of claim 1, wherein the hollow elongated casing is formed as a tube.

5. The gas sampling instrument of claim 4, wherein the sample intake opening is formed on a cylindrical side of the tube.

6. The gas sampling instrument of claim 5, wherein the width of the elongated slit is constant along the second length.

7. The gas sampling instrument of claim 1, wherein the width of the elongated slit is variable along the second length.

8. The gas sampling instrument of claim 1, wherein the sample intake opening forms an extended two-dimensional surface.

9. The gas sampling instrument of claim 1, wherein the hollow elongated casing is bent to sample in two or more dimensions.

10. The gas sampling instrument of claim 1, wherein one or more layers of the membrane have chemically-specific transfer properties.

11. The gas sampling instrument of claim 1, wherein the at least one port is configured to communicate vacuum pressure to the cavity to draw the sample gas from the cavity.

12. The gas sampling instrument of claim 11, wherein the at least one port is arranged on one of the longitudinal ends of the hollow elongated casing.

13. A leak detection assembly for detecting a leak source, the leak detection assembly comprising:

a gas sampling instrument for collection of a sample gas from at least a portion of a plume of gas, the gas sampling instrument comprising (i) a hollow elongated casing having a sidewall and a cavity, the cavity defined within the hollow elongated casing, the sidewall at least partially enclosing the cavity, the hollow elongated casing having a first length defined between longitudinal ends of the hollow elongated casing, (ii) a sample intake opening defined in the sidewall to receive the sample gas into the cavity, the sample intake opening formed as an elongated slit having a second length and a width, the second length extending between the longitudinal ends of the hollow elongated casing, wherein the second length of the elongated slit is greater than the width of the elongated slit, (iii) a membrane secured to the sidewall with a seal around the sample intake opening for passing the sample gas through the membrane into the cavity, and wherein the membrane is configured to act as a flow regulator that restricts a volume of flow of the sample gas into the cavity along the second length of the sample intake opening to balance the flow of the sample gas entering the cavity, and (iv) a port arranged in fluid communication with the cavity to provide passage for the sample gas; and a gas analysis system coupled with the port of the gas sampling instrument for receiving the sample gas from the cavity for analysis to detect the leak source.

14. The leak detection assembly of claim 13, further comprising a vacuum pump coupled between the port of the gas sampling instrument and the gas analysis system to draw the sample gas from the cavity.

15. The leak detection assembly of claim 13, wherein the hollow elongated casing is mounted on a vehicle at an angle such that flow delay in the cavity is compensated for by forward motion of the vehicle.

16. The leak detection assembly of claim 13, wherein the gas analysis system is further configured to analyze the sample gas to characterize the leak source.

17. A method of detecting a leak source, the method comprising:

mounting a gas sampling instrument for collection of a sample gas from at least a portion of a plume of gas to a vehicle, the gas sampling instrument comprising (i) a hollow elongated casing having a sidewall and a cavity, the cavity defined within the hollow elongated casing, the sidewall at least partially enclosing the cavity, the hollow elongated casing having a first length defined between longitudinal ends of the hollow elongated casing, (ii) a sample intake opening defined in the sidewall, the sample intake opening formed as an elongated slit having a second length and a width, the second length extending between the longitudinal ends of the hollow elongated casing, wherein the second length of the elongated slit is greater than the width of the elongated slit, and (iii) a membrane secured to the sidewall with a seal around the sample intake opening, and wherein the membrane is configured to act as a flow regulator that restricts a volume of flow of the sample gas into the cavity along the second length of the sample intake opening to balance the flow of the sample gas entering the cavity; and moving the vehicle and the mounted gas sampling instrument through a geographic area to collect the sample gas by passing the sample gas through the membrane into the cavity; and analyzing the collected sample gas to detect the leak source.

18. The method of claim 17, further comprising applying vacuum pressure to the cavity of the gas sampling instrument to draw the sample gas through the membrane into the cavity.

* * * * *